United States Patent
Morita et al.

(10) Patent No.: US 7,084,254 B2
(45) Date of Patent: Aug. 1, 2006

(54) TI-4 PROTEIN DERIVED FROM TRIATOMA INFESTANS EXHIBITING ACTIVITY TO INHIBIT PLATELET AGGREGATION

(75) Inventors: Akihiro Morita, Tsu (JP); Haruhiko Isawa, Tsu (JP); Masao Yuda, Tsu (JP); Yuki Orito, Suzuka (JP); Yasuo Chinzei, Tsu (JP)

(73) Assignee: Mie University, Tsu (JP)

( * ) Notice: Subject to any disclaimer, the term of this patent is extended or adjusted under 35 U.S.C. 154(b) by 173 days.

(21) Appl. No.: 10/401,141

(22) Filed: Mar. 28, 2003

(65) Prior Publication Data

US 2004/0072194 A1 Apr. 15, 2004

(30) Foreign Application Priority Data

Oct. 2, 2002 (JP) .................................. 2002-289564

(51) Int. Cl.
- *C07K 1/00* (2006.01)
- *C07K 14/00* (2006.01)
- *C07K 17/00* (2006.01)

(52) U.S. Cl. ....................................................... 530/350

(58) Field of Classification Search ................. 530/350, 530/324, 412; 514/12; 435/7.1, 69.1, 25.2
See application file for complete search history.

(56) References Cited

FOREIGN PATENT DOCUMENTS

JP 7-506959 8/1995

*Primary Examiner*—Robert A. Wax
*Assistant Examiner*—Robert Mondesi
(74) *Attorney, Agent, or Firm*—Buchanan Ingersoll PC

(57) ABSTRACT

The present invention provides Ti-4 protein, which is a protein obtained from salivary gland of *Triatoma infestans*, and the present invention provides Ti-4 gene encoding the protein. As the Ti-4 protein exhibits inhibitory activity on platelet aggregation, a medicine comprising the Ti-4 protein as an active ingredient will serve as a platelet aggregation inhibitor possibly effective for prevention and treatment of myocardial infarction, pulmonary infarction and cerebral infarction. Moreover, the Ti-4 protein will also serve as a highly prospective lead compound in the development of novel platelet aggregation inhibitors.

3 Claims, 2 Drawing Sheets

FIG. 1

```
        10        20        30        40        50        60
GCAAATTTTACTCTTCCAACATGAAGATGATTATTTCTCTGACATTTCTTGGAATACTGA
                 M  K  M  I  I  S  L  T  F  L  G  I  L  M 70        80        90       100       110       120
TGCTTGCATTTGCAGAGGTTAACTCTGAAACATGCACACTTATGGAAGCTGCGAAAAACT
 L  A  F  A  E  V  N  S  E  T  C  T  L  M  E  A  A  K  N  F 130       140       150       160       170       180
TTGATGAAAACAAGTATTTCAACATTCCTCTTGCGTATGCGACACATTCGAAGAATCGAG
  D  E  N  K  Y  F  N  I  P  L  A  Y  A  T  H  S  K  N  R  E 190       200       210       220       230       240
AGCCAGAAACAAATGTGTGCCGAGAATATAGTACTGCAAGAGGACCAGATGGCAAGACAG
  P  E  T  N  V  C  R  E  Y  S  T  A  R  G  P  D  G  K  T  V 250       260       270       280       290       300
TTACAACTTTCACAATTAAAGATAAGACACTTACTTCTGCTGTCAAATGTACCAATACGC
  T  T  F  T  I  K  D  K  T  L  T  S  A  V  K  C  T  N  T  P 310       320       330       340       350       360
CCATACCTGGTAGTAACGGCCAGTTTTCTTCAGATTGCGAACTATCAGCTGGCAATAGGA
  I  P  G  S  N  G  Q  F  S  S  D  C  E  L  S  A  G  N  R  I 370       380       390       400       410       420
TCACAGTAACTACATCAATTCTTGCTACAGACAATGAAAAATATGCTATACTTCAAAGAT
  T  V  T  T  S  I  L  A  T  D  N  E  K  Y  A  I  L  Q  R  C 430       440       450       460       470       480
GCCCTACGTCTGGACCAGGTAATATTTTGGTATTGCAAACGAATAAAAATGGCGTAGAAC
  P  T  S  G  P  G  N  I  L  V  L  Q  T  N  K  N  G  V  E  Q 490       500       510       520       530       540
AAGGAGTTCAAAATTATTTTAATCAAAAAGGTTGGGATATAAGCACATGGCTTTCCAGAA
  G  V  Q  N  Y  F  N  Q  K  G  W  D  I  S  T  W  L  S  R  T 550       560       570       580       590       600
CCACTGTTGGTTGTTGAAACATCCAGAACTAAACTTGAAAAAGAAAAATATAAAGAATT
  T  V  G  C  *

610       620       630       640       650
ATTATTTTAAATAAACTGGCATTAAAAGCAAAAAAAAAAAAAAA
```

TI-4 PROTEIN DERIVED FROM TRIATOMA INFESTANS EXHIBITING ACTIVITY TO INHIBIT PLATELET AGGREGATION

BACKGROUND OF THE INVENTION

1. Field of the Invention

The present invention relates to Ti-4 protein, which is a protein derived from salivary gland of *Triatoma infestans* (an assassin bug) exhibiting activity to inhibit platelet aggregation, and to a gene encoding the Ti-4 protein.

2. Description of the Related Art

With progression of aging of society, treatment of adult diseases as a social problem is becoming more important. What is the most important for the welfare of such aging society is treatment and prevention of symptoms related to adult diseases, particularly cardiovascular disorders resulting from vascular sclerosis such as hypertension, pulmonary hypertension, myocardial infarction, cerebral infarction, pulmonary infarction and vascular spasms followed by subarachnoid hemorrhage. Such vascular disorders can be prevented and treated by administration of vasodepressors, blood coagulation inhibitors and platelet aggregation inhibitors to the patients. The known peptide having an anticoagulant activity which may be used as a medicine for treating such vascular disorders includes hirudine, a peptide isolated from salivary gland of leech. Hirudine is an anticoagulant peptide isolated from salivary gland of assassin bugs and it exhibits anti-thrombic activity. Ti-4 protein of this invention and a gene encoding the protein are novel. However, general knowledge on physiologically active substances isolated from salivary glands of assassin bugs are described as reviews in the following scientific journals:

(1) Ribeiro, J. M., "Role of saliva in blood-feeding by arthropods", Annu. Rev. Entomol., 1987, vol.32, p463–478

(2) Basanova, A. V., Baskova, I. P., and Zavalova, L. L., "Vascular-platelet and plasma hemostatis regulators from bloodsucking animals" Biochemistry, 2002, vol67, p143–150

However, hirudine has some problems when applied as a medicine, those are, synthesis of hirudine is difficult, and it has some adverse side-effects. To achieve large amount of production of the compound to be used as a medicine in safely, it is necessary to solve the above problems. Thus, isolation of a protein whose synthesis is easy and capable of inhibiting the aggregation of platelets without causing any notable side-effects has been needed. If such a protein were produced, it would be a useful lead compound in the production of an anticoagulant, and be highly promising in the development of new medicines.

SUMMARY OF THE INVENTION

An object of the present invention is to provide a protein exhibiting activity to inhibit platelet aggregation isolated from salivary gland of *Triatoma infestans*, a blood-sucking insect. Another object of the present invention is to provide a method to achieve production of the protein in large amount, utilizing the system of baculovirus.

To achieve the above objects, the present application provides following inventions. This invention provides Ti-4 protein derived from *Triatoma infestans*, consisting of an amino acid sequence represented by amino acids Nos. (−22)-156 shown in SEQ ID No. 1 of the sequence listing. Other proteins consisting of an amino acid sequence in which a part of above-mentioned amino acid sequence is deleted, substituted, or another amino acid sequence is added to the above-mentioned amino acid sequence are also included in this invention, so far as exhibiting the activity to inhibit platelet aggregation.

This invention further provides Ti-4 protein derived from *Triatoma infestans*, consisting of an amino acid sequence represented by amino acids Nos. 1–156 shown in the SEQ ID No. 1 of the sequence listing. Other proteins consisting of an amino acid sequence in which a part of above-mentioned amino acid sequence is deleted, substituted, or another amino acid sequence is added to the above-mentioned amino acid sequence are also included in this invention, so far as the exhibiting the activity to inhibit platelet aggregation.

This invention further provides Ti-4 gene derived from *Triatoma infestans*, consisting of a base sequence represented by bases Nos. 1–644 shown in the SEQ ID No. 2 of the sequence listing. Other genes consisting of a base sequence in which a part of above-mentioned base sequence is deleted, substituted, or another base sequence is added to the above-mentioned base sequence are also included in this invention, so far as encoding proteins exhibiting the activity to inhibit platelet aggregation.

Furthermore. this invention provides a platelet aggregation inhibitor containing the above-mentioned protein as an effective ingredient.

BRIEF DESCRIPTION OF THE DRAWINGS

FIG. 1 is a figure showing the amino acid sequence of the Ti-4 protein, and the base sequence of the gene encoding the protein.

DESCRIPTION OF THE PREFERRED EMBODIMENTS

Figure 2:
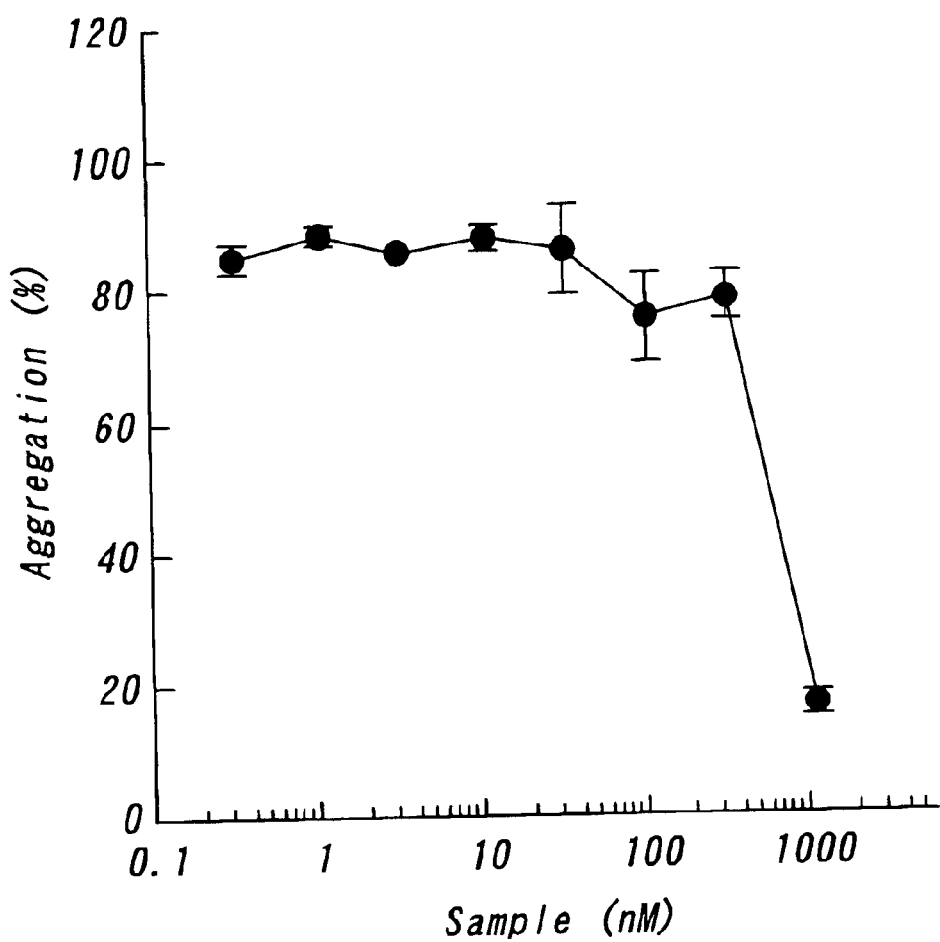
FIG. 2 is a graph illustrating the effect of Ti-4 protein on collagen-induced platelet aggregation.

The salivary glands derived from blood-sucking insects and mites contain substances having specific activities toward blood or blood vessels. Therefore, the present inventors identified an active substance having inhibitory effect to platelet aggregation, which is derived from salivary gland of such an insect. Then the inventors achieved isolation and purification of the substance, and further analyzed on the properties of the active substance. In a subsequent study, the inventors achieved cDNA cloning of the gene. Moreover, the inventors developed a method for production of the protein having the activity to inhibit platelet coagulation in a large scale, utilizing the system of baculovirus.

In concrete, the inventors paid attention to *Triatoma infestans* (Ti), which is a blood-sucking insect, and tried to isolate a protein exhibiting inhibitory activity on platelet aggregation derived from the insect. Salivary glands were removed from approximately 40 individuals of *Triatoma infestans*, total mRNA was extracted from the salivary glands, dsDNA was synthesized using poly(A)⁺mRNA as a template by reverse transcriptase, then cDNA library of the salivary gland was constructed by inserting the dsDNA into a transfer vector. From cDNA library of the Ti salivary gland, colonies were picked up at random and their base sequences were determined. The inventors sequenced on 550 colonies, they picked up cDNAs containing secretion signal and excluded overlapping cDNAs. As a consequence 44 cDNAs were obtained and total base sequences of them were determined. FIG. 1 shows base sequence of the Ti-4 gene thus obtained and amino acid sequence of the Ti-4 protein encoded by the gene.

Out of them, transfer vector constructs were prepared on 16 cDNAs to achieve protein expression in an expression system using baculovirus (AcNPV). The viruses were transfected with the construct, and viral clones failing to form apocytes, namely clones expressing proteins encoded by the inserts, were isolated. Expression of the protein was confirmed by SDS-PAGE, and the protein was isolated and purified by HPLC based on gel filtration chromatography and ion exchange chromatography, then Ti-4 protein according to this invention was obtained. Then, investigation of the protein according to this invention thus obtained was performed on its effect toward platelet aggregation.

The substance of the target was added to washed human platelets, and collagen was added to induce platelet aggregation. Ten minutes later, the light transmission of the sample was measured, and then inhibitory effect of the substance on the platelet aggregation was investigated. As a consequence, the Ti-4 protein inhibited collagen-induced platelet aggregation in dose-dependent manner. From this result, it was concluded that the Ti-4 protein according to this invention exhibited the effect to inhibit platelets aggregation, that is, the protein would be effective as a platelet aggregation inhibitor. Therefore, the Ti-4 protein will be effective as an active ingredient in medicines for treatment or prevention of myocardial infarction, pulmonary infarction and cerebral infarction.

The Ti-4 protein is defined by the amino acid sequence consisting of amino acids Nos. (−22)-156 shown in the SEQ ID No. 1 of the sequence listing. In this specification, the protein consisting of an amino acid sequence in which a part of said amino acid sequence represented SEQ ID NO: 1 in the sequence listing is deleted, substituted or added with another amino acid sequence means a protein consisting of an amino acid sequence in which 20 or less, preferably 10 or less, and more preferably 5 or less amino acids of the sequence is deleted, substituted or added to the amino acid sequence represented by SEQ ID NO: 1 in the sequence listing. Moreover, such protein exhibits homology 95% or more, preferably 97% or more and still preferably 99% or more with the amino acid sequence represented by SEQ ID NO: 1 in the sequence listing. Such polypeptide is also within the range of this invention so far as it exhibits function as Ti-4 protein of inhibiting platelet aggregation. Meanwhile, in the SEQ ID NO: 1 in the sequence listing, the region corresponding to amino acids Nos. −22 to −1 represent a signal peptide. The peptide received processing to yield a mature protein consisting of 156 represented by amino acids Nos. 1–156.

Moreover, the Ti-4 gene codes for the Ti-4 protein described above, and it consists of the base sequence represented by bases Nos. 1–644 shown in the SEQ ID No. 2 of the sequence listing. The region corresponding to bases Nos. 21–554 represents an open reading frame, and encodes the above protein. According to technique of gene recombination, artificial modification can be achieved at a specific site of basic DNA, without alteration or with improvement of basic characteristic of said DNA. Concerning a gene having native sequence provided according to this invention or modified sequence different from said native sequence, it is also possible to perform artificial modification such as insertion, deletion or substitution to obtain gene of equivalent or improved characteristic compared with said native gene. Moreover, a gene with such mutation is also included in the range of this invention.

That is, the gene consisting of a base sequence in which a part of said gene represented by base sequence represented by SEQ ID NO: 2 in the sequence listing is deleted, substituted or added with another base sequence means a gene consisting of a base sequence in which 20 or less, preferably 10 or less, and more preferably 5 or less bases of the sequence is deleted, substituted or added to the base sequence represented by SEQ ID NO: 2 in the sequence listing. Moreover, such gene exhibits homology 95% or more, preferably 97% or more and still preferably 99% or more with the base sequence represented by SEQ ID NO: 2 in the sequence listing. Such gene is also within the range of this invention so far as it encodes a protein exhibiting function as Ti-4 protein of inhibiting platelets aggregation. In addition, such gene hybridizes with the base sequence represented by SEQ ID No.2 in the sequence listing under a stringent condition.

The condition for hybridization can be selected by a skilled artisan ad libitum. For example, hybridization can be performed by the following procedure. DNA molecules or RNA molecules to be tested are transferred onto a membrane, then the membrane is hybridized with a labeled probe in a proper hybridization buffer. The hybridization buffer may comprise, for example, 5×SSC, 0.1 (weight)% N-lauroylsarcosine, 0.02 (weight)% SDS, 2 (weight)% of blocking reagent for nucleic acid hybridization, and 50% formamide. The blocking reagent for nucleic acid hybridization may comprise, for example, a buffer (pH 7.5) containing 0.1M maleic acid and 0.15M sodium chloride and commercially available blocking reagent for hybridization dissolved into the buffer at the concentration of 10%. The 20×SSC solution may comprise 3M sodium chrolide and 0.3M citrate, and the SSC solution may be preferably utilized at the concentration of 3 to 6×SSC, more preferably at the concentration of 4 to 5×SSC.

The temperature for hybridization may preferably be 40 to 80° C., more preferably be 50 to 70° C., further more preferably be 55 to 65° C. Incubation may be performed from several hours to overnight, then washed by a washing buffer. The temperature for washing may preferably be room temperature, more preferably it may be the temperature used for hybridization. The formulation for the washing buffer may preferably comprise 6×SSC and 0.1% (weight %) SDS, more preferably may comprise 4×SSC and 0.1% (weight %) SDS, further preferably may comprise 2×SSC and 0.1% (weight %) SDS, more further preferably may comprise 1×SSC and 0.1% (weight %) SDS, most preferably may comprise 0.1×SSC and 0.1% (weight %) SDS. The membrane may be washed by such washing buffer, then DNA molecule or RNA molecule may be distinguished by the hybridization with the labeled probe.

It is possible to produce Ti-4 protein according to this invention in a large scale, utilizing baculovirus expression system in which cDNA encoding the Ti-4 protein is inserted. An exemplary production method will be mentioned below. The Ti-4 protein is allowed to express in BmN4 culture cells (silkworm cell) or in silkworm larvae, utilizing *Bombyx mori* nuclear polyhedral virus (BmNPV). The extract derived from the culture medium or from the body fluid of the silkworm larvae is subjected to chromatography to isolate the target protein. Alternatively, cDNA encoding the Ti-4 protein can be inserted into *Autographa californica* nuclear polyhedral virus (AcNPV), and the Ti-4 protein is allowed to express in Sf9 cells derived from *Spodoptera frugiperda* or in Tn5 cells derived from *Trichoplusia ni*. Supernatant of the culture medium is subjected to chromatography in the same manner to isolate the target protein.

The Ti-4 protein according to this invention can be produced in a large scale, utilizing an *E. coli* expression system in which cDNA encoding the Ti-4 protein is inserted.

For such a purpose, cDNA encoding the Ti-4 protein can be amplified; and the cDNA can be inserted into a plasmid such as pMAL-c2g to construct a vector for expression of a fusion protein with maltose binding protein (MBP). E. coli is transformed with the expression vector, cultivated in a medium containing IPTG to induce expression of the Ti-4 protein fused with MBP in the E. coli. The E. coli strains preferred for such a purpose include BL21 strain, for example. The MBP fused Ti-4 protein induced in E. coli bodies can be recovered by disrupting the cell bodies. The MBP fused Ti-4 protein thus recovered can be purified by affinity chromatography utilizing an amylose resin.

The Ti-4 protein of this invention having inhibitory effect on platelet aggregation can be produced in a large scale by; identification, isolation and purification of the active substance exhibiting inhibitory effect on platelet aggregation derived from salivary gland of a blood-sucking insect, cloning of the cDNA encoding the active substance, and expressing the protein in a baculovirus expression system. If the active site responsible for the inhibitory effect on platelet aggregation will be determined on the protein and progression on structural analysis of the protein will be achieved, the active substance will be produced through conventional synthetic procedure using technique of molecular designing.

Moreover, the Ti-4 protein according to this invention will be quite valuable as a prospective lead compound in the development of novel medicines having an inhibitory effect on platelet aggregation. Furthermore, the structure of the Ti-4 protein can be modified in various manners to develop novel compounds exhibiting higher inhibitory potency on platelet aggregation. Thus, the Ti-4 protein according to this invention provides a physiologically active substance that becomes the basis for such investigation. Furthermore, it is quite useful as a lead compound useful for further development of novel platelet aggregation inhibitors.

EXAMPLES

The present invention will be illustrated below by means of examples. However, the present invention is not limited in any way to those examples.

Procedure for Gene Isolation

Salivary glands were removed from thorax of Triastoma infestans. The mRNA was extracted from the salivary glands and purified using Microprep mRNA purification kit (Amersham Pharmacia). Using the mRNA as a template, cDNA library of the salivary glands was constructed using Superscript Plasmid System (Life Technology). The clones (approximately 550 clones in total) were randomly picked up from this library and plasmids were extracted and purified using QiAPrep Spin Miniprep kit (Qiagen). The base sequence of the cDNA inserted in the plasmid was determined with ABI PRISM 310 genetic analyzer (PE Biosystems). Then the inventors analyzed on the base sequence of the cDNA thus determined, using a Genetyx ver. 8.5 (Software Development). As a result, it was revealed that four cDNA clones were possessing an identical base sequence, and it was designated to be Ti-4 gene.

Massive Expression of the Recombinant Protein and Purification of the Protein

The full length cDNA of Ti-4 gene was amplified by PCR and it was inserted into BamHI restriction site of plasmid pAcYM1 to produce a transfer vector, and then it was purified using Plasmid Mini kit (Qiagen). The plasmid vector was introduced into insect culture cells (Sf-9) using Baculogold Linearized Baculovirus DNA (Phaemingen) to produce recombinant baculoviruses. The recombinant viruses were allowed to infect another insect culture cells (Tn-5) and massive expression of the recombinant Ti-4 was achieved. The recombinant Ti-4 protein was secreted into the culture medium and the recombinant protein was purified via two steps of purification, that is, cation ion exchange chromatography with MONO S (Amersham Pharmacia) and gel-filtration chromatography with TSK2000SW (Toso). The purified product was used in the subsequent experiment.

Aggregation of Blood Platelets

Platelet aggregation was determined using washed human platelets by turbidimetric assay method. In other word, 50 µl of washed human platelets ($6.0 \times 10^5$/ml) was added into 40 µl of solution comprising the purified Ti-4 protein dissolved into a buffer solution containing 50 mM Tris-HCl (pH 7.4) and 150 mM NaCl, and the mixture was incubated at 37° C. After 10 minutes of incubation, 10 µl of collagen (Chronolog) solution (20 µg/ml) was added to it, and the mixture was further incubated for ten minutes. The light transmission of the solution was measured at 600 nm using Micro Plate reader MPR-A4i (Toso).

FIG. 2 shows the effect of Ti-4 protein on collagen-induced platelet aggregation. FIG. 2 shows that the Ti-4 protein inhibits platelet aggregation in a dose dependent manner. This demonstrates that the Ti-4 protein isolated from salivary gland of Triatoma infestans can inhibit collagen-induced platelet aggregation.

The present invention provides Ti-4 protein, a novel protein derived from Triatoma infestans, and a gene coding for the Ti-4 protein. The Ti-4 protein has an inhibitory activity on platelet aggregation, therefore, a medicine comprising the Ti-4 protein as an active ingredient will serve as a platelet aggregation inhibitor possibly effective for prevention and treatment of myocardial infarction, pulmonary infarction and cerebral infarction. Moreover, the Ti-4 protein will also serve as a highly prospective lead compound in the development of new platelet aggregation inhibitors.

What is claimed is:

1. An isolated and purified protein derived from *Triatoma infestans* consisting of the amino acid sequence of following (a), or (b):
   (a) an amino acid sequence represented by amino acids Nos. −22–156 of SEQ ID NO:1;
   (b) an amino acid sequence exhibiting at least 95% homology with amino acid sequence (a), wherein amino acid sequence (b) inhibits platelet aggregation.

2. An isolated and purified protein derived from *Triatoma infestans* consisting of the amino acid sequence of following (a), or (b):
   (a) an amino acid sequence represented by amino acids Nos. 1–156 of SEQ ID NO:1;
   (b) an amino acid sequence exhibiting at least 95% homology with amino acid sequence (a), wherein amino acid sequence (b) inhibits platelet aggregation.

3. A platelet aggregation inhibitor containing the protein according to claim 2 as an active ingredient.

* * * * *

SEQUENCE LISTING

```
<160> NUMBER OF SEQ ID NOS: 2

<210> SEQ ID NO 1
<211> LENGTH: 178
<212> TYPE: PRT
<213> ORGANISM: Triatoma infestans
<220> FEATURE:
<221> NAME/KEY: SIGNAL
<222> LOCATION: (1)...(22)

<400> SEQUENCE: 1

Met Lys Met Ile Ile Ser Leu Thr Phe Leu Gly Ile Leu Met Leu Ala
```

-continued

```
                -20                 -15                 -10
Phe Ala Glu Val Asn Ser Glu Thr Cys Thr Leu Met Glu Ala Ala Lys
 -5                   1                   5                   10
Asn Phe Asp Glu Asn Lys Tyr Phe Asn Ile Pro Leu Ala Tyr Ala Thr
                 15                   20                   25
His Ser Lys Asn Arg Glu Pro Glu Thr Asn Val Cys Arg Glu Tyr Ser
                 30                   35                   40
Thr Ala Arg Gly Pro Asp Gly Lys Thr Val Thr Thr Phe Thr Ile Lys
                 45                   50                   55
Asp Lys Thr Leu Thr Ser Ala Val Lys Cys Thr Asn Thr Pro Ile Pro
 60                   65                   70
Gly Ser Asn Gly Gln Phe Ser Ser Asp Cys Glu Leu Ser Ala Gly Asn
 75                   80                   85                   90
Arg Ile Thr Val Thr Thr Ser Ile Leu Ala Thr Asp Asn Glu Lys Tyr
                 95                  100                  105
Ala Ile Leu Gln Arg Cys Pro Thr Ser Gly Pro Gly Asn Ile Leu Val
                110                  115                  120
Leu Gln Thr Asn Lys Asn Gly Val Glu Gln Gly Val Gln Asn Tyr Phe
                125                  130                  135
Asn Gln Lys Gly Trp Asp Ile Ser Thr Trp Leu Ser Arg Thr Thr Val
                140                  145                  150
Gly Cys
155
```

<210> SEQ ID NO 2
<211> LENGTH: 644
<212> TYPE: DNA
<213> ORGANISM: Triatoma infestans

<400> SEQUENCE: 2

```
gcaaatttta ctcttccaac atgaagatga ttatttctct gacatttctt ggaatactga      60
tgcttgcatt tgcagaggtt aactctgaaa catgcacact tatggaagct gcgaaaaact     120
ttgatgaaaa caagtatttc aacattcctc ttgcgtatgc gacacattcg aagaatcgag     180
agccagaaac aaatgtgtgc cgagaatata gtactgcaag aggaccagat ggcaagacag     240
ttacaacttt cacaattaaa gataagacac ttacttctgc tgtcaaatgt accaatacgc     300
ccatacctgg tagtaacggc cagttttctt cagattgcga actatcagct ggcaatagga     360
tcacagtaac tacatcaatt cttgctacag acaatgaaaa atatgctata cttcaaagat     420
gccctacgtc tggaccaggt aatatttttgg tattgcaaac gaataaaaat ggcgtagaac     480
aaggagttca aaattatttt aatcaaaaag gttgggatat aagcacatgg ctttccagaa     540
ccactgttgg ttgttgaaac atccagaact aaacttgaaa aagaaaaat ataagaatt     600
attattttaa ataaactggc attaaaagca aaaaaaaaa aaaa                       644
```